(12) United States Patent
Qasem et al.

(10) Patent No.: US 9,314,524 B2
(45) Date of Patent: Apr. 19, 2016

(54) TOPICAL FORMULATIONS OF FLUCYTOSINE

(75) Inventors: Jaber Qasem, Loveland, OH (US); Raymond H. Farmen, Portage, MI (US); Kenneth Phelps, Cincinnati, OH (US)

(73) Assignee: CALLA THERAPEUTICS LLC, Cincinnati, OH (US)

( * ) Notice: Subject to any disclaimer, the term of this patent is extended or adjusted under 35 U.S.C. 154(b) by 883 days.

(21) Appl. No.: 12/342,518

(22) Filed: Dec. 23, 2008

(65) Prior Publication Data

US 2009/0170876 A1    Jul. 2, 2009

Related U.S. Application Data

(60) Provisional application No. 61/009,626, filed on Dec. 31, 2007.

(51) Int. Cl.
*A61K 31/4965* (2006.01)
*A61K 45/06* (2006.01)

(52) U.S. Cl.
CPC .............. *A61K 45/06* (2013.01); *A61K 31/4965* (2013.01)

(58) Field of Classification Search
CPC . A61K 31/4965; A61K 2300/00; A61K 45/06
See application file for complete search history.

(56) References Cited

U.S. PATENT DOCUMENTS

| | | | |
|---|---|---|---|
| 4,946,870 A | 8/1990 | Partain et al. | |
| 5,120,718 A | 6/1992 | Goldman et al. | |
| 5,160,737 A | 11/1992 | Friedman et al. | |
| 5,174,475 A | 12/1992 | Day et al. | |
| 5,599,534 A | 2/1997 | Himmelstein et al. | |
| 5,733,572 A | 3/1998 | Unger et al. | |
| 5,952,334 A | 9/1999 | Calderon et al. | |
| 5,980,948 A | 11/1999 | Goedemoed et al. | |
| 6,159,491 A | 12/2000 | Durrani | |
| 6,165,484 A | 12/2000 | Raad et al. | |
| 6,165,997 A | 12/2000 | Cohen et al. | |
| 6,180,623 B1 | 1/2001 | Kruse et al. | |
| 6,432,415 B1 | 8/2002 | Osborne et al. | |
| 6,476,063 B2 | 11/2002 | Zhang et al. | |
| 6,486,165 B2 | 11/2002 | Zhang et al. | |
| 6,492,351 B1 | 12/2002 | Zhang et al. | |
| 6,555,566 B2 | 4/2003 | Ponikau | |
| 6,562,363 B1 | 5/2003 | Mantelle et al. | |
| 6,638,528 B1 | 10/2003 | Kanios | |
| 6,645,506 B1 | 11/2003 | Farmer | |
| 6,733,751 B2 | 5/2004 | Farmer | |
| 6,770,306 B1 | 8/2004 | Zeng | |
| 6,835,536 B2 | 12/2004 | Krieger et al. | |
| 6,864,278 B2 | 3/2005 | Balkovec et al. | |
| 6,875,740 B1 | 4/2005 | Ikeda et al. | |
| 6,905,692 B2 | 6/2005 | Farmer | |
| 6,911,211 B2 | 6/2005 | Eini et al. | |
| 2002/0052404 A1* | 5/2002 | Hunter et al. | 514/449 |
| 2002/0197314 A1 | 12/2002 | Rudnic et al. | |
| 2003/0007948 A1 | 1/2003 | Hedgpeth | |
| 2003/0032605 A1 | 2/2003 | Raad et al. | |
| 2003/0099707 A1 | 5/2003 | Rudnic et al. | |
| 2003/0147953 A1 | 8/2003 | Rudnic et al. | |
| 2003/0152623 A1 | 8/2003 | Bromberg et al. | |
| 2003/0157138 A1 | 8/2003 | Eini et al. | |
| 2003/0180352 A1 | 9/2003 | Patel et al. | |
| 2003/0181384 A1 | 9/2003 | Podolsky | |
| 2003/0203023 A1 | 10/2003 | Rudnic et al. | |
| 2004/0018241 A1 | 1/2004 | Houze et al. | |
| 2004/0157837 A1 | 8/2004 | Serbedzija et al. | |
| 2004/0185068 A1 | 9/2004 | Yu et al. | |
| 2004/0191276 A1 | 9/2004 | Muni | |
| 2004/0191284 A1 | 9/2004 | Yu et al. | |
| 2004/0198633 A1 | 10/2004 | Antonov | |
| 2004/0208860 A1 | 10/2004 | Farmer | |
| 2004/0229822 A1 | 11/2004 | Zeng | |
| 2004/0241099 A1 | 12/2004 | Popp et al. | |
| 2004/0247674 A1 | 12/2004 | Haapakumpu et al. | |
| 2005/0031547 A1 | 2/2005 | Tamarkin et al. | |
| 2005/0069566 A1 | 3/2005 | Tamarkin et al. | |
| 2005/0074414 A1 | 4/2005 | Tamarkin et al. | |
| 2005/0075407 A1 | 4/2005 | Tamarkin et al. | |
| 2005/0096388 A1 | 5/2005 | Hunter et al. | |
| 2005/0101635 A1 | 5/2005 | Hunter et al. | |
| 2005/0107291 A1 | 5/2005 | Hunter et al. | |
| 2005/0129736 A1 | 6/2005 | Hunter et al. | |

FOREIGN PATENT DOCUMENTS

WO    WO 2008/066618    *    6/2008    ........... A61K 31/496

OTHER PUBLICATIONS

Salager, Surfactants Types and Uses, FIRP Booklet, 2002, pp. 1-50.*

* cited by examiner

*Primary Examiner* — Savitha Rao
(74) *Attorney, Agent, or Firm* — Jenei LLC

(57) ABSTRACT

The invention relates to topical formulations of flucytosine which demonstrate a clear advantage over currently available therapeutic regimens for the treatment and maintenance of fungal infections, particularly vulvovaginal candidiasis. The invention provides compositions which solve the long-standing need for antimicrobial agents which treat effectively resistant strains of *Candida* spp., especially *C. albicans*, *C. glabrata*, and *C. tropicalis*, and which pose limited risk of side effects, adverse reactions, or the development of resistant pathogens. The invention provides novel topical formulations of flucytosine designed to allow the active drug to act at the local application area, but which inhibit or moderate transdermal or transmucosal absorption of the drug, thus limiting systemic exposure.

11 Claims, No Drawings

TOPICAL FORMULATIONS OF FLUCYTOSINE

RELATED APPLICATIONS

This application claims the benefit of U.S. Provisional Application No. 61/009,626, filed Dec. 31, 2007. The entire disclosure of which is hereby incorporated by reference.

TECHNICAL FIELD

The present invention relates generally to formulations of Flucytosine and more specifically to formulations for using flucytocine compositions.

BACKGROUND

Vulvovaginal candidiasis (VVC) is one of the most common conditions affecting women. VVC is an inflammatory condition caused by *Candida* spp. Hypothesized risk factors include pregnancy, diabetes mellitus, contraceptive method, antibiotics, tight fitting clothing, sexual practices, feminine hygiene and diet. According to the Centers for Disease Control and Prevention (CDC), an estimated 75% of women will have at least one episode of VVC, and 40% to 45% will have two or more episodes in their lifetime (CDC Treatment Guidelines, Vulvovaginal Candidiasis, 2002). In addition, approximately 10-20% of women suffer from Complicated VVC, which is characterized by 1) infections which may be due to non-albicans species of *Candida;* 2) occur on a recurrent basis (>4 episodes/12 months); or 3) are more severe than Uncomplicated VVC (CDC Treatment Guidelines, supra; Sobel J., 1999, *Drug Resist Update,* 2:148-152). While some percentage of chronic recurring VVC may be explained by genetic predisposition, little is known about risk factors for acquiring a first or second episode.

Despite newer therapeutic agents, attempts at better compliance (such as tablet formulations and short-term treatments) and adoption of suppressive maintenance therapies, the effective management of complicated VVC remains problematic. Currently available antifungals, available by either prescription or over the counter (OTC), are indicated for the treatment of Uncomplicated acute VVC (characterized by sporadic, infrequent attacks of mild-to-moderate severity due to *C. albicans;* CDC Treatment Guidelines, supra; Sobel 1999, supra). However, the use of these products in women with Complicated VVC has proven to be unsuccessful.

Attempts to increase therapeutic efficacy in women with Complicated VVC have entailed the use of maintenance suppressive azole regimens. Examples of azole antifungal agents include fluconazole, butoconizole, itraconazole, clotrimazole, econazole, miconazole, oxiconazole, terconazole, tioconazole, and ketoconazole. Long-term studies in women with recurrent disease indicate that at least half of the patients who remain in clinical and mycological remission while on maintenance therapy will rapidly relapse following cessation of therapy (Sobel J. et al, 2004; *N. Engl. J. Med.,* 351:876-883; Balkis M. et al, 2002, *Drugs,* 62:1025-1040; Fidel P. et al, 1996, *Clin. Microbiol. Rev.,* 9:335-348; Sobel J. et al, 1998, *Mycoses,* 41 Suppl. 2:18-22). A substantial amount of evidence exists confirming this high rate of clinical failure to control disease in women with Complicated VVC treated with these currently available antifungal products (Sobel, J. 2004, supra; Balkis, M. 2002, supra; Fidel, P. 1996, supra; Sobel, J. 1998, supra; MacNeill C. et al, 2001, *Curr. Womens Health Rep.* 1:31-35; Berg A et al, 1984, *J. Amer. Med. Assn.,* 251:620-625; McCormack W. et al, 1994, *Sex Transm. Dis.,* 21:63-64.) Treatment of Uncomplicated VVC with non-azole antifungals, such as the polyene antimicrobials nystatin and amphotericin B (AmB) has been somewhat successful. However, severe issues relating to the ability of the fungal pathogens to acquire resistance to currently-used medication is an escalating problem.

The widespread reports of fluconazole resistance in *Candida* species has prompted the study of species distribution of vulvovaginal candidiasis and their in vitro susceptibility against current antifungal agents. A total of 314 women with vaginal infection were studied. Yeasts were isolated from 104 patients with vulvovaginal candidiasis. The following species were identified: *C. albicans* 87.5%, *C. glabrata* 8.6% and 3.9% included *C. krusei, C. famata,* and *C. tropicalis.* The minimal inhibitory concentration (MIC) was determined for nystatin, isoconazole, fluconazole and ketoconazole, using a broth micro dilution method based on National Committee on Clinical Laboratory Standards (NCCLS) procedure. Although most of the isolates were *C. albicans,* the high percentage of *C. glabrata* recovered suggests the need to identify the yeasts isolated. Fluconazole resistant *C. albicans* were isolated in 13.46% of the cases. (Saporiti, A. et al, 2001, *Rev. Argent. Microbiol.;* 33(4):217-22).

Other workers isolated and identified the yeast species in the vagina of patients treated in the gynecology clinic and tested in vitro activities of fluconazole and itraconazole against 227 clinical yeast isolates by the NCCLS micro dilution method. *C. albicans* (87.6%) was the most frequently identified species followed by *C. glabrata* (6.2%) and *C. krusei* (2.2%). Almost thirteen percent of yeast strains were resistant to fluconazole and 18.5% were resistant to itraconazole. Cross-resistance analyses of *C. albicans* isolates revealed that fluconazole resistance and itraconazole resistance were also associated with decreased susceptibilities to other azole derivatives mainly to ketoconazole and miconazole. At the same time no cross-resistance to polyene antibiotics amphotericin B and nystatin was observed. These results support the notion that antifungal agents used to treat vaginitis may be contributing to the drug resistance problem by promoting cross-resistance to a range of clinically used antifungals. (Sojakova, M. et al, 2004, *Mycopathologia, February;*157(2):163-9).

In another study, the in vitro susceptibility to amphotericin B, fluconazole, itraconazole and ketoconazole of 545 *Candida* strains from patients treated at the University Hospital of the Canaries was determined by means of a micro dilution test. The distribution of the species was as follows: *Candida albicans* (342), *Candida tropicalis* (70), *Candida glabrata* (68), *Candida parapsilosis* (65). Of *Candida albicans* isolates, 8.5% and 7.6% showed resistance to itraconazole and fluconazole respectively. Of *C. tropicalis* isolates 34.3%, 27.1% and 2.9% were resistant to itraconazole, fluconazole and ketoconazole respectively. For *C. glabrata,* 10.3% and 4.4% of the isolates under study demonstrated resistance to fluconazole and itraconazole respectively. Only 4.6% and 1.5% of *C. parapsilosis* isolates demonstrated resistance to fluconazole and itraconazole respectively. *C. tropicalis* was the most resistant strain and *C. parapsilosis* the most sensitive. The greatest percentages of resistance in vitro were seen with the triazoles (Arias, A. et al, 1994, Mycoses; 37(7-8): 285-9.)

In attempts to find antifungal agents which are capable of treating candidiasis without imparting serious side-effects or drug resistance, clinicians have investigated topical applications of the powerful antifungal flucytosine (5-fluorocytosine, 5-FC, or 4-amino-5-fluoropyrimidin-2(1H)-one) to patients with candidiasis refractory to treatment with either azole antifungals or AmB.

Flucytosine, marketed in the U.S. as the oral formulation ANCOBON® only for treatment of serious systemic infections of *Candida* and *Cryptococcus*, has the potential to cause serious side effects when taken orally. The ANCOBON® package insert (Physicians Desk Reference 2001, 55:1530) contains explicit warnings concerning the systemic use of the drug. ANCOBON® must be given with extreme caution to patients with impaired renal function. Since ANCOBON® is excreted primarily by the kidneys, renal impairment may lead to accumulation of the drug. ANCOBON® serum concentrations should be monitored to determine the adequacy of renal excretion in such patients. Dosage adjustments should be made in patients with renal insufficiency to prevent progressive accumulation of active drug. ANCOBON® must be given with extreme caution to patients with bone marrow depression. Patients may be more prone to depression of bone marrow function if they: 1) have a hematologic disease, 2) are being treated with radiation or drugs which depress bone marrow, or 3) have a history of treatment with such drugs or radiation. Bone marrow toxicity can be irreversible and may lead to death in immunosuppressed patients. Frequent monitoring of hepatic function and of the hematopoietic system is indicated during therapy. Among side effect and adverse reactions to systemic flucytosine are the following: cardiac arrest, myocardial toxicity, respiratory arrest, chest pain, dyspnea, rash, pruritus, urticaria, photosensitivity, nausea, emesis, abdominal pain, diarrhea, anorexia, dry mouth, duodenal ulcer, gastrointestinal hemorrhage, acute hepatic injury with possible fatal outcome in debilitated patients, hepatic dysfunction, jaundice, ulcerative colitis, bilirubin elevation, increased hepatic enzymes, azotemia, creatinine and BUN elevation, crystalluria, renal failure, anemia, agranulocytosis, aplastic anemia, eosinophilia, leukopenia, pancytopenia, thrombocytopenia, ataxia, hearing loss, headache, paresthesia, parkinsonism, peripheral neuropathy, pyrexia, vertigo, sedation, convulsions, confusion, hallucinations, psychosis, fatigue, hypoglycemia, hypokalemia, weakness, allergic reactions, and Lyell's syndrome. Thus, in the administration of flucytosine for the treatment of fungal infection, there is a concern that improper systemic levels of the drug could lead to deleterious side effects. It has been demonstrated, for example, that plasma levels of greater than 100 mg/L in human patients has led to bone marrow depression (leucocytopenia, thrombocytopenia, and pancytopenia) and hepatotoxicity (Kauffmann, C. et al 1977; Antimicrob. Agents Chemother. 11:244-247).

There are also concerns that systemic use of flucytosine might give rise to flucytosine-resistant pathogens. Previous studies have indicated that flucytosine should be avoided in antimicrobial therapy. Previous workers warn that flucytosine usage is limited due to the development of resistance to the drug and due to its narrow spectrum of activity (Alexis, B. et al, U.S. Pat. No. 6,818,231). Others state that flucytosine has limited clinical utility, as clinical isolates of Candida develop resistance to flucytosine, and consequently, antibiotic therapy for candidiasis is highly variable from one individual to the next and resolution of fungal lesions is primarily associated with improved immunocompetence, as opposed to direct antifungal therapy (O'Donnell, U.S. Pat. No. 5,455,028). It is reported that flucytosine resistance is common, especially when used as monotherapy for *candida*, and that adverse effects are displayed as well (Aerts et al, US Pat. Appl. Publ. 20040253224). One report cautions that flucytosine is indicated only for serious microbial infections, and that mitigation of the usefulness of this powerful drug is to be avoided by sparing use. (Normark, S. et al, 1972, *Antimicrob. Agents Chemother.;* 2:114).

It has been shown that sensitization to flucytosine depends upon the oral dose and duration of treatment (Hope, W. et al, 2006; Antimicrob. Agents Chemother., 50:3680). Also, it is known that up to 30% of patients who receive oral flucytosine therapy develop resistance to the drug (Perea, S. et al, 2002; Clin. Infect. Dis., 35:1073-1080). Indeed, the use of flucytosine oral therapy has been restricted by the high prevalence of resistance and by the speed at which oral flucytosine therapy develops resistant organisms after treatment (Sangland, D. et al, 2002; Lancet Infectious Diseases, 2:73-85).

The topical administration of flucytosine has been shown in isolated studies to be an effective treatment for candidiasis. An early study assessed the efficacy of flucytosine topically applied to intertriginous candidiasis (disease between folds or juxtaposed surfaces of the skin). A formulation containing 10% flucytosine was compounded using Ancotil (a 10 g/l flucytosine for infusion solution available in the U.K.) into a cream base. The composition of the formulation was not disclosed. Clinicians found that the compounded flucytosine and nystatin gel were equally effective at treating the infection, and that no side effects were observed. No attempts were reported to assess or control the transdermal or transmucosal delivery of flucytosine to the blood. (Gisslen, H. et al, 1974, *Dermatologia,* 148:362-365.)

Since the only approved dosage form of flucytosine currently available in the U.S. is ANCOBON® formulated in an oral capsule, clinicians have resorted to crushing capsule contents, and mixing the resultant powder into a suitable cream base in order to incorporate flucytosine into a formulation suitable for topical administration to VCC patients.

A method for preparing a flucytosine formulation for topical application to the vagina has been described (Horowitz B., 1986; *J. Reprod. Med.* 31:821-824). A study was performed which evaluated topical flucytosine therapy for chronic recurrent *Candida tropicalis* infections. In this study, patients identified as having *C. tropicalis* vaginitis were begun on topical miconazole nitrate 2% or topical clotrimazole cream 1%, one application nightly for seven nights. If this therapy failed, ketoconazole, 200-mg/d for 14 days, was begun. Following this, those patients who continued to have symptoms and to culture *C. tropicalis* were given an intravaginal dose of flucytosine cream. The dose of 1 g daily was chosen based upon the oral dosing of 2.5 g to 7.5 g a day (ANCOBON® Labeling).

ANCOBON®, 1 g per applicator, was compounded into a cold cream base. Flucytosine cream was created by opening fourteen 500-mg capsules of ANCOBON® into a mortar and reducing this to a fine powder. The powder was levigated with glycerin to form a smooth paste. The levigated mixture was added to hydrophilic ointment base or cold cream, q.s., to 45 g. This mixture was blended until smooth, and two 2 ounce ointment tubes were filled. The patient was instructed to insert the mixture into a 6.4 g vaginal applicator and dispense the cream vaginally.

A total of 936 patients were involved in the study. Of the 962 cultures prepared, 267 were positive for *C. albicans* and 25% for *C. tropicalis*. Forty-one patients yielded 68 cultures positive for *C. tropicalis*. Twenty-eight patients were initially treated with 2% miconazole nitrate, one application each night for seven nights. Thirteen patients were treated for seven nights with one application nightly of 1% clotrimazole cream.

Twelve patients treated with 2% miconazole nitrate cream had recurrences, and three treated with clotrimazole cream had recurrences. Two miconazole nitrate patients and 1 clotrimazole patient were treated secondarily with ketoconazole, 200-mg, for 14 days. In all three of these patients, the infection recurred.

After treatment 15 uncured patients remained. All 15 patients with recurring candidiasis were then treated with compounded flucytosine vaginal cream. Patients applied 5 g of flucytosine cream (approximately 1 g flucytosine) vaginally every night for 14 nights. This treatment resulted in clinical cure in 14 patients. The 15th patient remained uncured, but she reported that her recurrences were less frequent. The cream was well tolerated (no reported symptoms of irritation, inflammation and burning). In this study, no attempts were reported to assess or control the transdermal or transmucosal delivery of flucytosine to the blood.

A very limited study (n=3) was conducted in which AmB and flucytosine were compounded together in lubricating jelly, and this mixture of antifungals was applied topically to women suffering from azole-resistant infection of *C. glabrata*. The clinicians reported a formulation of 12.5% flucytosine and 1.25% AmB in lubricating gel, applied topically, was effective in treating the disease (White, D. et al, 2001, *Sex. Trasm. Inf.*, 77:212-213.) No attempts were reported to assess or control the transdermal or transmucosal delivery of flucytosine to the blood.

In a retrospective review, case records of 141 women with positive vaginal cultures of *C. glabrata* were inspected to evaluate the treatment outcome and safety of therapy with boric acid or flucytosine vaginal cream. The review demonstrated that a boric acid regimen of 600-mg day for 2 to 3 weeks achieved clinical and mycological success in 47 of 73 symptomatic women (64%). No advantage was observed in extending therapy for 14 to 21 days. Intravaginal flucytosine cream was offered to 30 patients, 26 of whom had previously received boric acid therapy, with either short-term failure or relapse. The flucytosine cream was prepared as described by Horowitz (1986, supra.) Patients applied 5 g of flucytosine vaginal cream (equivalent to 1 g flucytosine) vaginally every night for 14 nights. Intravaginal flucytosine cream administered nightly for 14 days was associated with a successful outcome in 27 of 30 women (90%). One patient was lost to follow-up. The remaining 2 patients were treated with oral itraconazole and intravaginal nystatin resulting in a cure in one patient. All patients completed and tolerated vaginal flucytosine therapy (Sobel J., 2003; *Am. J. Obstet. Gynecol.* 189:1297-1300). In this study, no attempts were reported to assess or control the transdermal or transmucosal delivery of flucytosine to the blood.

Thus, these limited prior studies provide conflicting suggestions that although topically applied anti-mycotics including flucytosine can potentially be effective in the treatment of fungal infections, flucytosine use should be avoided due to its propensity for the formation of drug-resistant fungal strains and deleterious side effects. Furthermore, previous efforts have failed to provide an effective, simple, cost-effective, easy to administer, highly patient-compliant, safe, and effective means to treat serious fungal disease. Specifically, there is an outstanding unmet need for highly effective agents for treating VVC and other fungal infections, but which present limited potential for side effects and adverse reactions. More specifically, there is an outstanding unmet need for agents to treat VCC and other fungal diseases which have a high degree of clinical effectiveness against strains of *Candida* spp. which have developed resistance to commonly used and commonly available antifungal drugs. The present invention discloses embodiments which provides solutions to these problems.

SUMMARY

Embodiments of the present invention relate to topical formulations of flucytosine which provide significantly improved results compared to currently available therapeutic regimens for the treatment of fungal infections and prophylaxis against re-infection, particularly VVC. The exemplary embodiments of the present invention provide compositions which solve the long-standing need for antimicrobial agents which treat effectively resistant strains of *Candida* spp., especially *C. albicans, C. glabrata*, and *C. tropicalis*, and which pose limited risk of side effects, adverse reactions, or the development of resistant pathogens. In addition, exemplary embodiments of the present invention provide novel topical formulations of flucytosine designed to allow the active drug to act at the local application area, but which inhibit or moderate transdermal or transmucosal absorption of the drug, thus limiting systemic exposure. One aspect of the present invention is to provide formulations of flucytosine in which the minimization of systemic absorption of the drug is controlled by careful choice of the nature and relative amount of excipient ingredients. Another aspect of the present invention is to provide flucytosine compositions for topical use which retain therapeutically effective drug levels at the site of infection, so that the drug concentration is not depleted by systemic absorption and diffusion of the drug away from the site of application. Exemplary embodiments of the present invention provide formulations in which a significant portion of the active drug is ionized, and therefore rendered less capable of transdermal or transmucosal penetration. In addition, exemplary embodiments of the present invention provide formulations wherein the concentration of active drug is lower than had been previously considered effective, thereby delivering an effective local dose while limiting the potential for systemic absorption. Exemplary embodiments of the present invention provide formulations of flucytosine paired with another antifungal drug to potentially maximize clinical efficacy.

DETAILED DESCRIPTION

As used above, and throughout the description of the invention, the following terms, unless otherwise indicated, shall be understood to have the following meanings:

"Patient" means a mammal including a human.

"Therapeutically effective dose" means an amount of flucytosine effective for treating fungal diseases or conditions, thus producing the desired therapeutic effect, such amount determined by practitioners with skill in the art.

"Treat" or "treatment" or "treating" mean to lessen, eliminate, inhibit, improve, alter, or prevent a disease or condition by topical administration of flucytosine formulations of the present invention.

"Pharmaceutically acceptable" means compounds, methods, procedures, formulations, addition salts, solutions, preparations, and routes of administration known by those with skill in the art to be proper and safe in the practice of administering biologically active medicaments to patients.

"Hydrophilicity modulators" means compounds utilized in formulations described herein which possess chemical structures which enable non-covalent attractive interactions with other compounds of the formulation of similar hydrophilicity.

"pH modulators" means additive compounds or solutions of compounds which cause the pH of the formulations described herein to be within the ranges described. "pH modulators" may also be organic acids which form an addition salt with flucytosine. Employment of pH modulators allow the formulation of therapeutically effective compositions of the invention which possess pH values within the ranges described.

"Topical composition" means a cream, gel, ointment, lotion, levigate, solution, paste, bioadhesive, salve, milk, impregnated pad, spray, suspension, foam, or the like containing an active drug which is applied to body surfaces such as the skin, mucous membranes, vagina, oral cavity, and the like in order to distribute the active drug upon the area of administration.

"Preservative" means a compound which preserves, protects, or otherwise stabilizes one or more components of the formulation by virtue of its characteristics including, but not limited to, antimicrobial activity, anti-oxidant activity, and chemical stability.

"Carrier" means a compound or mixture of compounds into which the active drug and excipients of the invention are dissolved, suspended, levigated, intermixed, homogenized, or emulsified to provide a composition of the invention.

"Transdermal penetration enhancers" mean compounds which alter the physical characteristics of the skin in order to facilitate permeation of chemical substances through the skin or mucosa and into the blood system.

"Compatible emulsifying agents" mean compounds which allow the components of the formulations of the invention to form stable emulsions without interfering with the express designed properties of the formulations as disclosed herein.

"Dermal absorption modulators" means compounds or solutions of compounds which inhibit, retard, lessen, or prevent the permeation of flucytosine through the skin or mucosa and into the blood system.

It is understood that, throughout the discussion, that "%" and "per cent" mean per cent by weight (% w/w) unless otherwise indicated.

Exemplary embodiments of the invention relate to formulations containing flucytosine which are designed to maximize the effect of the drug at the local area of administration while minimizing or limiting the amount of drug which is taken up systemically via transcutaneous permeation. Embodiments of the invention accomplish local delivery of the drug without extensive permeation by taking advantage of the structure of the skin and mucosa, and by careful choice of the components of the composition. Embodiments of the invention in which systemic absorption of the drug is minimized by the nature of the composition offer the advantage that, because the drug is prevented from dispersing throughout the circulation, local levels remain high at the site of infection. This allows for a shorter duration of therapy. The composition of one exemplary embodiment of the present invention is comprised of about 0.5% flucytosine. Application, for example, of a 2.5 g dose to a 100 $cm^2$ area would provide a local drug level of about 1.25 $mg/cm^2$. The composition of another exemplary embodiment of the present invention is comprised of about 20% flucytosine. Application of, for example, a 7.5 g dose to a 100 $cm^2$ area would provide a local drug level of about 15 $mg/cm^2$. The choice of composition is to be made by a practioner skilled in the art and will depend on several factors, including the site of application, severity of disease, age and general health of the patient, and co-existing disease conditions. Thus, compositions of the present invention can provide therapeutically effective treatment of disease by delivering a local drug level in the range of about 1.25 $mg/cm^2$ to about 15 $mg/cm^2$. Exemplary embodiments of the present invention provide compositions of flucytosine which are designed to prevent high plasma drug levels by limiting flucytosine absorption after topical application. Prevention of high systemic flucytosine levels leads to reduced undesirable side effects. Limitation of systemic exposure to flucytosine also minimizes the potential for the development of resistant organisms. The composition of another exemplary embodiment of the invention comprises from about 0.5% to about 10% flucytosine, an emulsifier, a preservative, and citrate buffer to provide a formulation pH of about 4. At this pH, transdermal penetration of flucytosine is inhibited, and plasma blood levels will remain low after topical administration. In this exemplary embodiment, blood levels will not exceed 100 mg/L, which is considered the concentration limit above which side effects and adverse events become increasingly more likely.

It has long been known that many lipophilic chemicals may cross the skin or mucosal barrier and enter systemic circulation, but polar and ionized molecules are impeded by the nature of the skin and mucosa from such penetration. This phenomenon was first recognized in 1957 (Shore, P. et al, 1957; *J. Pharmacol. Expt. Therap.*, 199(3):361-369) and has been the basis of success for the effective transdermal or transmucosal delivery of several lipophilic drugs (for example, fentanyl, nitroglycerin, estradiol, ethynyl estradiol, testosterone, clonidine, and norethindrone acetate). Moreover, it was shown that the free base of both fentanyl and sufentanyl are responsible for facile skin penetration while the permeation of the ionic protonated form of these drugs were impeded by the skin barrier (*Pharm. Res.* 1990 7(8): 842-847.) This "pH partition" has guided the awareness of which drugs might effectively be administered by topical means. Many drugs are organic acids or bases. A general rule is that only nonionized (lipid soluble) drugs pass quickly through membranes. Ionized species are too polar to pass easily. Thus, the rate of permeation of organic acids and bases will be determined by the gradient for the nonionized form across the membrane. This will be governed by the pK and by the pH. This is the "pH partition hypothesis" and is based on the Henderson-Hasselbalch equation.

$$pH = pK + \log [A]/[HA^+]$$

The pK not only has a marked effect upon what is absorbed and what is not absorbed, it also determines equilibrium positions across the membranes. This is particularly true when the pH values on opposite sides of the membrane are very different. Absorption of the drug across a membrane will continue until the driving force is zero. Since most drugs only cross membranes when they are nonionized, this means that zero driving force is achieved when the nonionized drug concentrations on the two sides are equal. This means that the total drug concentrations on each side may be very different even at equilibrium. In transdermal drug delivery practice, however, non-ionized compounds which permeate the skin enter the "sink" of systemic circulation and are effectively removed from the local equilibrium. In the transmucosal delivery of drugs, non-ionized compounds may permeate the mucosa more rapidly and thus enter the systemic circulation.

The problem of slow transdermal or transmucosal penetration of lipophilic or unionized drug molecules across the skin and mucosa has given rise to the development of "transdermal permeation enhancers" which impart a modification of the skin and mucosa to facilitate absorption of drugs normally excluded from the permeation pathway. "Penetration enhancement" or "permeation enhancement" refers to an increase in the permeability of the skin or mucosal tissue to a selected pharmacologically active compound such that the rate at which the compound permeates through the skin or mucosal tissue is increased. These modifiers alter, among other possible parameters, the diffusibility or solubility of drugs in the skin and mucosa. Terpenes, fatty acids, fatty acid esters, dimethyl sulfoxide, laurocapram, glyceryl monooleate, lauryl acetate, 2-n-nonyl-1,3-dioxolane, and other compounds have been identified as transdermal permeation enhancers (Finnin, B. et al, 1999, *J. Pharm. Sci.,* 88(10): 955-958). Several terpenes which act as transdermal permeation enhancers have been evaluated, and include terpinolene, α-phellandrene, ocimene, myrcene, (1R)-(−)-myrtenal, (S)-(−)-perillaldehyde, carvacrol, thymol, (R)-(−)-carvone, (1R)-(−)-myrtenol, (−)-α-thujone, (R)-(+)-pulegone, (+)-dihydrocarvone, (−)-carveol, citral, (−)-isopulegol, (+)-dihydrocarveol, (−)-dihydrocarveol, (S)-(−)-citronellal, geraniol, nerol, (±)-linalool, menthone, β-citronellol, L-(−)-menthol, cyclohexanemethanol, A-humulene, (−)-α-cedrene, (+)-β-cedrene, (+)-aromadendrene, (+)-longifolene, (−)-trans-caryophyllene, (−)-caryophyllene oxide, (−)-epiglobulol, (−)-guaiol, (+)-cedrol, (−)-isolongifolol, (−)-α-santonin, octisalate, (+)-cedryl acetate, retinol, phytol, squalene, (±)-α-bisabolol, famesol, (±)-nerolidol, eucarvone, retinoic acid, and β-carotene (Kang, L. et al. 2007; *J. Controlled Release,* 120:211-219).

It is emphasized that the exemplary formulations of the present invention rely upon manipulating the ionized state of the flucytosine drug molecule and the hydrophilic environment of the formulation to control the extent of local absorption of the drug, and that the exemplary compositions of the present invention minimize or exclude the use of transdermal permeation enhancers to minimize or prevent systemic absorption of flucytosine, rather than enhance transdermal penetration as in conventional topical compositions. In one exemplary embodiment, such enhancers, as cited above or their equivalents, are expressly excluded from the formulations of the invention.

In some exemplary embodiments of the invention, dermal absorption modulators are used to control (e.g., reduce) the permeation of flucytosine across the skin and mucosal membrane into the systemic circulation. Unlike transdermal permeation enhancers, dermal absorption modulators function to control the environment within the formulation in such a way as to promote the optimal local action of flucytosine at the point of infection while minimizing the transdermal or transmucosal delivery of the drug. Exemplary dermal absorption modulators include pH modulators and hydrophilicity modulators.

One aspect of the present invention is to control the extent of ionization of flucytosine in the formulation by utilizing pH modulators. In some exemplary embodiments, pH modulators function by establishing the pH of the formulation to be within the ranges disclosed. For example, buffers may be incorporated into the composition. Choice of buffer or mixture of buffers will dictate the pH of the formulation, and therefore the extent of flucytosine ionization. In other exemplary embodiments, agents such as organic acids may be chosen as pH modulators. A discrete addition salt of flucytosine and organic acid may be formed and incorporated into the formulation. Exemplary embodiments incorporating pH modulators allow the control of the amount of ionized flucytosine in the composition, therefore allowing control of the systemic absorption of flucytosine while enabling the drug to act locally at infected tissues.

Some exemplary embodiments of the invention rely upon establishing a pH of about 3.5 to about 4.5, an optimal range to control the concentration of ionized flucytosine within the formulation. The normal vaginal pH is between about 3.8 and about 4.5, and the pH of these embodiments is chosen to provide a composition which minimizes systemic absorption of the drug but which is not irritating to the patient. Another exemplary pH range is between about 3.8 and about 4.2.

It has been shown that the rate of release of a basic drug (timolol maleate) from microspheres fabricated to simulate human skin increased linearly with the increase of pH within the microspheres (Sutinen, R. et al 1995; *J. Controlled Release,* 33:163-71). Timolol maleate, initially present as 100% ionized, equilibrates into ionized (salt) and unionized (free base) forms in the presence of buffer (Henderson-Hasselbalch equation, supra). It is the free base which diffuses through the membrane. These findings reinforce the notion that the unionized form of the drug molecule passes through the membrane (skin) much faster than the ionized form. Consequently, it is predicted that release of timolol from the microsphere would be slowed with a decrease of pH within the microsphere. In the case of the present invention, the intent of some exemplary embodiments is to control the pH of the milieu of the formulation so that the ratio of ionized and unionized forms of flucytosine is known. The concentration of the free base of flucytosine, able to penetrate the skin and mucosa, can therefore be controlled, and thus the unique composition of the formulation allows practitioners of the invention to provide therapeutic amounts of drug locally while limiting systemic uptake.

TABLE 1

Ratio of flucytosine free base (5FC) to protonated flucytosine (5FC+) at various pH values.

| pH | 5FC/5FC+ | % 5FC | % 5FC+ |
|---|---|---|---|
| 5 | 54.95 | 98.21 | 1.79 |
| 4.9 | 43.65 | 97.76 | 2.24 |
| 4.8 | 34.67 | 97.20 | 2.80 |
| 4.7 | 27.54 | 96.50 | 3.50 |
| 4.6 | 21.88 | 95.63 | 4.37 |
| 4.5 | 17.38 | 94.56 | 5.44 |
| 4.4 | 13.80 | 93.24 | 6.76 |
| 4.3 | 10.96 | 91.64 | 8.36 |
| 4.2 | 8.71 | 89.70 | 10.30 |
| 4.1 | 6.92 | 87.37 | 12.63 |
| 4 | 5.50 | 84.60 | 15.40 |
| 3.9 | 4.37 | 81.36 | 18.64 |
| 3.8 | 3.47 | 77.62 | 22.38 |
| 3.7 | 2.75 | 73.36 | 26.64 |
| 3.6 | 2.19 | 68.63 | 31.37 |
| 3.5 | 1.74 | 63.47 | 36.53 |
| 3.4 | 1.38 | 57.99 | 42.01 |
| 3.3 | 1.10 | 52.30 | 47.70 |
| 3.2 | 0.87 | 46.55 | 53.45 |
| 3.1 | 0.69 | 40.89 | 59.11 |
| 3 | 0.55 | 35.46 | 64.54 |
| 2.9 | 0.44 | 30.39 | 69.61 |
| 2.8 | 0.35 | 25.75 | 74.25 |
| 2.7 | 0.28 | 21.59 | 78.41 |
| 2.6 | 0.22 | 17.95 | 82.05 |
| 2.5 | 0.17 | 14.81 | 85.19 |
| 2.4 | 0.14 | 12.13 | 87.87 |
| 2.3 | 0.11 | 9.88 | 90.12 |
| 2.2 | 0.09 | 8.01 | 91.99 |
| 2.1 | 0.07 | 6.47 | 93.53 |
| 2 | 0.05 | 5.21 | 94.79 |

In one exemplary embodiment of the invention, the pH of the formulation is 3.5, providing about a 1.7:1 ratio favoring the unionized flucytosine, which comprises about 63% of flucytosine. In another exemplary embodiment, the pH is selected to be 4.0, to provide 84.6% unionized flucytosine. In still another exemplary embodiment, selection of pH 3.0 provides 35.5% unionized flucytosine. In still yet another exemplary embodiment, selection of pH 2.0 provides 5.2% unionized flucytosine. Selection of the pH of the formulation allows the modulation of the concentration of flucytosine available for permeation. The pH of the formulation may be controlled by adding one or more buffers to the composition. Components of buffers and methods of their preparation are well-known in the art. Buffers of the present invention include, but are not limited to, buffers of formic acid, acetic acid, phosphoric acid, boric acid, citric acid, chloroacetic acid, oxalic acid, succinic acid, glutaric acid, adipic acid, pimelic acid, sebacic acid, azelic acid, subaric acid, maleic acid, fumaric acid, benzoic acid, phthalic acid, and ascorbic acid. In some exemplary embodiments, mixtures of polybasic carboxylic acids and buffers are used, said polybasic carboxylic acids including, but not limited to, oxalic acid, succinic acid, glutaric acid, adipic acid, pimelic acid, sebacic acid, azelic acid, subaric acid, maleic acid, and fumaric acid, and said buffers including, but not limited to, buffers of acids such as acetic acid, phosphoric acid, boric acid, citric acid, chloroacetic acid, and the like. Exemplary compositions of the present invention may be adjusted with buffers to pH value ranges of about 1.0 to about 5.0, alternatively about 2.5 to about 5.0, and still alternatively to about 3.5 to 4.5. Methods of preparation of buffers to the required pH value are known to those with skill in the art. Such preparation may be accomplished, for example, by the addition of mineral acid such as HCl to a solution of the acid to be buffered, such as citric acid to the endpoint of the desired pH as monitored, for example, by litmus paper or a pH meter.

In other exemplary embodiments of the invention, pH modulators are organic acids with varying degrees of hydrophilicity. In these exemplary embodiments, discrete addition salts of flucytosine with organic acids are formed, and incorporated into the formulation. These salts may be prepared, isolated, and purified by techniques well-known in the art. Alternatively, the salts may be formed in situ by techniques well-known in the art. It is known that addition salts, so-called ion pairs formed by such a salt formation, (flucytosine)$^+$ (organic acid)$^-$, have vastly different diffusion kinetics across membranes such as skin and mucosa than do the salts of flucytosine formed in a buffered system. If a more hydrophobic organic acid is selected, the net hydrophobicity of the ion pair increases, and the ion pair can more easily pass through the skin and mucosa. Conversely, if a more hydrophilic organic acid is chosen, the resulting ion pair has more hydrophilic character, and permeates slower. Selection of the organic acid as an ion pair partner imparts control over the rate of permeation of the salt, and thus of flucytosine (Neubert, R., 1989; *Pharm. Res.,* 6:743-747; Pardo, A. et al, 1992; *J. Pharm. Sci.* 81:990-995; Trotta, M. et al, 2003; *J. Controlled Release,* 86:315-321). The relative hydrophilicity of a organic acid ion-pair partner for flucytosine is known to those with skill in the art. Hydrophilicity may be judged by the logP of the organic acid, which may be measured by conventional means or may be calculated (by, for example, commercially available software such as ACD/logP available from ACD Laboratories, http://www.acdlabs.com). Lower logP values indicate higher hydrophilicity, whereas higher logP values indicate higher hydrophobicity. It is one aspect of the present invention that permeability of ion-paired forms of flucytosine can be controlled by choice of the organic acid ion-pair partner. Exemplary organic acid ion-pair partners of the present invention may include any pharmaceutically acceptable organic acid. Exemplary organic acid ion-pair partners of the present invention include, but not limited to, benzoic acid, phthalic acid, salicylic acid, propionic acid, butyric acid, valeric acid, acetic acid, formic acid, maleic acid, fumaric acid, methanesulfonic acid, glycine, alanine, lactic acid, malic acid, gluconic acid, tartaric acid, malonic acid, ethylenediamine tetraacetic acid, and nicotinic acid. Exemplary organic acid ion-pair partners of the present invention further include, but are not limited to, glycine, alanine, beta-alanine, threonine, serine, leucine, isoleucine, valine, sarcosine, glutamic acid, and aspartic acid. Exemplary organic acids suitable for use in the present invention are those with molecular weight less than 300 daltons and which are soluble in at least one of the components of the exemplary compositions of the present invention. Organic acids most suitable in the invention are those with logP in the range of about −3.5 to about 0.0. For example, organic acids most suitable for use in the invention include, but are not limited to, gluconic acid (logP=−3.18), methanesulfonic acid (logP=−1.89), tartaric acid (logP=−1.43), malic acid (logP=−1.26), glycine (logP=−1.03), lactic acid (logP=−0.70), and ethylenediamine tetraacetic acid (logP=−0.43). Organic acids not suitable for use in the invention are those with logP in the range of about 2.0 to about 8.5. For example, organic acids not suitable for use in the invention include caprylic acid (logP=+2.90), lauric acid (logP=+5.03), oleic acid (logP=+7.70) and steric acid (logP=+8.22). Organic acid − flucytosine addition salts may be prepared by methods known to those with skill in the art. An organic acid, for example methanesulfonic acid, might be dissolved in an organic solvent such as ethanol and the resulting solution might be added to a solution of flucytosine in an organic solvent such as ethanol. The resulting mixture might then be heated until homogeneous, then cooled and the addition salt isolated by means known in the art such as concentration of the solvent, or precipitation or crystallization of the salt by addition of a second organic solvent such as ether. It will be understood that the flucytosine addition salt is prepared by mixing equimolar amounts of flucytosine and organic acid. It will be appreciated that a flucytosine-organic acid salt may also be formed by mixing flucytosine and the organic acid in one or more of the components of the formulation, thus providing, when the formulation is complete, the same net effect as the stepwise process of forming a discrete flucytosine-organic acid salt which is subsequently mixed into one or more components of the formulation.

In other embodiments of the invention, the composition of the formulation is controlled by the addition of hydrophilicity modulators. Within the scope of the invention, hydrophilicity modulators assemble in a non-covalent way with flucytosine or a flucytosine salt, or a mixture of flucytosine and a flucytosine salt. In one aspect of the invention, hydrophilicity modulators added to the formulation cause an aggregation complex composed of the modulator and flucytosine to be formed in situ. Such aggregations may involve, among others, hydrophilic interactions and ionic interactions. In another aspect of the invention, aggregation complexes are formed by methods known in the art, isolated, and added to the formulation. Preformed aggregates include, but are not limited to, liposomes, inclusion complexes, and micelles. Aggregates of flucytosine and hydrophilic modulators within exemplary formulations of the present invention control the transcutaneous permeation of flucytosine. Exemplary hydrophilicity modulators of the present invention include, but are not limited to, surfactant molecules, cationic polymers, anionic polymers, polar block co-polymers, and amphiphilic molecules. Exemplary hydrophilicity modulators of the present invention include, but are not limited to, poly(lactic acid), poly(lysine), poly(arginine), poloxamers (for example PLURONIC (TM) block copolymers, Bayer Corporation), poly (epsilon-caprolactone), poly(ethylene glycol)-poly(lysine) block copolymers, phospholipids, polymers of 2-acrylamido-2-methylpropane sulfonic acid, aryl sulfonates, poly(dialkylamino)methacrylates, and poly(vinylpyridine).

In some exemplary embodiments of the present invention, the transcutaneous permeation of flucytosine into the systemic circulation is controlled by adjusting the concentration of flucytosine in the formulation to levels well below those taught in the earlier art. A therapeutically effective dose of a formulation of one exemplary embodiment of the present invention comprises about 0.3 g flucytosine. A therapeutically effective dose of a formulation of another exemplary embodiment of the present invention comprises about 0.5 g flucytosine. A therapeutically effective dose of a formulation of still another exemplary embodiment of the present invention comprises about 0.75 g flucytosine. A therapeutically effective dose of a formulation of still yet another exemplary embodiment of the present invention comprises about 1.0 g flucytosine. It will be appreciated that, according to exemplary embodiments of the present invention, formulations comprising dermal penetration modulators may employ higher concentrations of flucytosine with minimized risk of side effects, adverse reactions, or induced *Candida* resistance to flucytosine. Therefore, a therapeutically effective dose of a formulation of one exemplary embodiment of the present invention comprises about 1.5 g flucytosine. A therapeutically effective dose of a formulation of another exemplary embodiment of the present invention comprises about 2.0 g flucytosine. Prior work (supra) disclose an effective concentration of a flucytosine formulation to be 15.6%. In some exemplary embodiments of the present invention, the level of flucytosine is about 0.3%. In some exemplary embodiments of the present invention, the level of flucytosine is about 0.5%. In some exemplary embodiments of the present invention, the level of flucytosine is about 1.5%. In some exemplary embodiments the flucytosine level is about 10% of the formulation. It will be appreciated that, according to the exemplary embodiments of the present invention, formulations comprising dermal penetration modulators may employ higher concentrations of flucytosine with minimized risk of side effects, adverse reactions, or induced *Candida* resistance to flucytosine. Therefore, in some exemplary embodiments the flucytosine level is about 20% of the formulation.

One or more exemplary embodiments of the present invention also provide formulations which contain one or more additional antimicrobial agents. Exemplary additional antimicrobial agents include, but are not limited to, amorolfine, isoconazole, clotrimazole, econazole, miconazole, nystatin, terbinafine, bifonazole, amphotericin B, griseofulvin, ketoconazole, fluconazole, fezatione, ticlatone, tolnaftate, triacetin, zinc pyrithione, sodium pyrithione, butenafine, butoconazole, clioquinol, itraconazole, lanoconazole, neticonazole, tioconazole, polybiguanides, terconazole, ciclopirox olamine, boric acid, oxiconazole, and ketoconazole. The amount of additional antimicrobial agent added to formulations of the present invention depends upon the nature, potency, and toxicity of the antimicrobial, and the need of the patient, and can be judged by practitioners with skill in the art.

The present invention provides exemplary formulations of flucytosine for topical use. Formulations of the invention comprise flucytosine, one or more emulsifying agents, a preservative, a carrier, and one or more dermal absorption modulators. It is emphasized that the formulations of the invention do not incorporate transdermal permeation enhancers.

Flucytosine, the active pharmaceutical Ingredient, is widely available in GMP quality (e.g., Nantong Haiers Pharmaceutical Co. Ltd, Shanghai, China; Archimica, Flintshire, UK).

Suitable emulsifying agents within the scope of the invention are those which do not interfere with the control of the transdermal or transmucosal penetration of flucytosine according to the invention. Suitable emulsifying agents include, but are not limited to, polyoxyethylene oleyl ether, PEG-40 stearate, ceteareth-12, Eumulgin B-1 (Henkel), ceteareth-20, Eumulgin B-2 (Henkel), ceteareth-30, Lanette O (Henkel), glyceryl stearate Cutina GMS (Henkel), PEG-100 stearate, methyl myristate, isopropyl myristate, Arlacel 165, glyceryl stearate, PEG-100 stearate, steareth-2 and steareth-20, stearamidopropyl dimethylamine, behentrimonium methosulfate, dimethicone copolyol, Polysorbate 20 (Tween 20), Polysorbate 40 (Tween 40), Polysorbate 60 (Tween 60), Polysorbate 80 (Tween 80), lauramide DEA, cocamide DEA, and cocamide MEA, Phospholipid PTC, triethanolamine, alginate, carrageenan, Glucate DO, methylcellulose, polyvinyl alcohol, Cocamidopropyl phosphatidyl PG-dimonium chloride, Pemulen TR 1, Pemulen TR 2, Carbopol 1342, Carbopol 1382, Carbomer 1342, Carbomer 934, Carbomer 934P, Carbomer 940, Carbomer 941, Carbomer 974P, Carbomer 980, Carbomer 981, and their equivalents. Emulsifying agents which are not useful in the invention are those which interfere with the control (i.e. inhibition) of the absorption of flucytosine through the skin. For example, basic emulsifiers such as N-alkyl polymethylene diamines, ethoxylated alkylamines, and ethoxylated soy-amine base.

A preservative is a compound which preserves, protects, or otherwise stabilizes one or more components of the formulation by virtue of its characteristics including, but not limited to, antimicrobial activity, anti-oxidant activity, and chemical stability. Preservatives suitable for use in the compositions of the present invention include, but are not limited to, chloro-m-cresol, citric acid, disodium edetate, ethoxylated alcohol, glycerin, 1,2,6-hexanetriol, methylparaben, parabens, potassium sorbate, propyl gallate, propylene glycol, propylparaben, sodium bisulfite, sodium citrate, butylparaben, sodium metabisulfite, sorbic acid, tannic acid, zinc stearate, butylated hydroxytoluene, butylated hydroxyanisole, benzoic acid, salicylic acid, propylparaben, dichlorobenzyl alcohol, formaldehyde, alpha-tocopherol, sodium ascorbate, ascorbic acid, ascorbyl palmitate phenol, m-cresol, bisphenol, cetrimide, benzalkonium chloride, sorbic acid, polyquatemum-1, chlorobutanol, chlorhexidine, Dowcell 200 (Dow Chemical Co., Midland, Mich.), Glydant (dimethylol-25,5-dimethylhydantoin, Lonza, Inc, Fairlawn, N.J.), Germal 115 (imidazolidylurea, Sutton Laboratories, Chatham, N.J.), Germal II (diazolidinylurea, Sutton), sodium hydroxymethylglycinate, Buzan 1504 (dimethhydroxymethyl pyrazole, Buckman Labs, Memphis, Tenn.), phenoxyethanol, benzoyl peroxide and their equivalents.

Carriers and carrier components suitable for use in the compositions of the present invention are described, for example in various reference works such as Martindale—The Extra Pharmacopoeia, Pharmaceutical Press, London, 1993. Suitable carriers of the invention include, but are not limited to, glycerin, glycerol, propylene glycol, hexylene glycol, gelatin, urea, camauba wax, Brij 72, stearate NF, polysorbate 60, polyglyceryl-3-oleate, sorbitol solution (USP), microcrystalline wax, white petrolatum, xanthen gum, cetomacrogol 1000 BP, cetostearyl alcohol, PEG, cyclomethicone, demethiconol, dimethicone copolyol, hydroxyoctacosanyl hydroxy stearate, methoxy PEG-22/dodecylglycol copolymer, Carbomer 940 NF, docusate sodium, trolamine NF, Carbomer 934P, poyoxomer 407, triolein, egg yolk phospholipids, cold cream (USP), hydrophilic ointment (USP), an emulsion of mineral oil and purified water, purified water, and mixtures thereof.

Suitable exemplary formulations of the present invention may include a salve, cream, gel, ointment, lotion, levigate, solution, paste, foam, or suspension. In some exemplary embodiments of the present invention, the formulation is a cream. In some exemplary embodiments of the present invention, the formulation is a gel. In some exemplary embodiments of the present invention, the formulation is an ointment.

The exemplary embodiments of the present invention can be utilized to treat various fungal infections.

EXAMPLE 1

Aqueous Phase Preparation: In a suitable container, flucytosine, and propylene glycol are dissolved in 10-30 ml purified water at room temperature. Oil Phase Preparation: In a suitable container, white petrolatum, isopropyl myristate, Pemulen TR-2, Carpool 981, methylparapen, and propylparapen are added together, heated to 50-60° C. (or until melted) and mixed thoroughly. Final Cream Preparation: Once the oil phase is melted and mixed, the aqueous phase is added slowly under continuous mixing. After mixing the two phases, citrate Buffer is added to adjust the pH to 4.0. Finally, water is added to obtain the required volume.

| Excipient | Function | % w/w | Range % wt/wt |
|---|---|---|---|
| Flucytosine | API | 0.5 | 0.3-20.0 |
| Isopropyl Myristate | Oil Phase/ Emulsifying agent | 12 | 1.0-25.0 |
| White Petrolatum | Oil Phase | 4 | 1-10 |
| Propylene Glycol | Solvent/ Emulsifying agent | 3 | 1-10 |
| Pemulen TR-2 | Emulsion stabilizer | 0.3 | 0.1-5.0 |
| Carbopol 981 | Emulsifying agent | 0.1 | 0.05-5.0 |
| Methylparaben | Preservative | 0.17 | 0.05-0.5 |
| Propylparaben | Preservative | 0.05 | 0.05-0.5 |
| Examples: Citrate Buffer, Acetate Buffer, Phosphate Buffer | pH Modulator | qs pH ~4.0 | |
| Water | | q.s. ad 100 | |

EXAMPLE 2

Aqueous Phase Preparation: In a suitable container, flucytosine, benzoic acid and propylene glycol are dissolved in 10-30 ml Purified Water at room temperature. Oil Phase Preparation: In a suitable container, white petrolatum, isopropyl myristate, Pemulen TR-2, and Carpool 981, are added together, heated to 50-60° C. (or until melted), and mixed thoroughly. Final Cream Preparation: Once the oil phase is melted and mixed, the aqueous phase is added slowly under continuous mixing. After mixing the two phases, the citrate buffer is added to adjust the pH to 4.0. Finally water is added to obtain the required volume.

| Excipient | Function | % w/w | Range % wt/wt |
|---|---|---|---|
| Flucytosine | API | 0.5 | 0.3-20 |
| Isopropyl Myristate | Oil Phase/ Emulsifying agent | 12 | 1.0-25.0 |
| White Petrolatum | Oil Phase | 4 | 1-10 |
| Propylene Glycol | Solvent/Emulsifying agent | 3 | 1-10 |
| Pemulen TR-2 | Emulsion stabilizer | 0.3 | 0.1-5.0 |
| Carbopol 981 | Emulsifying agent | 0.1 | 0.05-5.0 |
| Benzoic Acid | Preservative | 0.2 | 0.05-0.5 |
| Examples: Citrate Buffer, Acetate Buffer, Phosphate Buffer | pH Modulator | qs pH ~4.0 | |
| Water | Aqueous Phase | q.s. ad 100 | |

All cited documents are incorporated herein by reference in their entirety for all purposes.

The specific examples and embodiments described herein are exemplary in nature and not intended to be limiting of the invention defined by the claims. Further embodiments and examples will be apparent to one of ordinary skill in the art in view of this specification and are within the scope of the claimed invention.

What is claimed is:

1. A topical composition for exterior treatment of vulvovaginal candidiasis comprised of flucytosine, a carrier, and poly(lactic acid),
wherein the flucytosine is selected from the group consisting of flucytosine, a flucytosine salt or a mixture thereof and is capable of forming ionized flucytosine;
wherein the poly(lactic acid) reduces permeation of flucytosine across skin and mucosal membrane;
wherein the carrier comprises a pH modulator suitable to establish a pH of the composition of between about 1 to about 5 to control the ratio of ionized flucytosine to unionized flucytosine within the composition and
wherein the topical composition is configured to minimize systemic absorption of the ionized flucytosine in the treatment environment.

2. The topical composition of claim 1 further comprising one or more additional agents selected from the group consisting of antimicrobial agents, dermal absorption modulators, hydrophilicity modulators, preservatives, buffers, carriers, and emulsifying agents.

3. The topical composition of claim 2 further comprising one or more preservatives selected from the group consisting of chloro-m-cresol, citric acid, disodium edetate, ethoxylated alcohol, glycerin, 1,2,6-hexanetriol, methylparaben, parabens, potassium sorbate, propyl gallate, propylene glycol, propylparaben, sodium bisulfite, sodium citrate, butylparaben, sodium metabisulfite, sorbic acid, tannic acid, zinc stearate, butylated hydroxytoluene, butylated hydroxyanisole, benzoic acid, salicylic acid, propylparaben, dichlorobenzyl alcohol, formaldehyde, alpha-tocopherol, sodium ascorbate, ascorbic acid, ascorbyl palmitate phenol, m-cresol, bisphenol, cetrimide, benzalkonium chloride, sorbic acid, polyquaternum-1, chlorobutanol, chlorhexidine, DOWICIL® 200 (Quaternium-15, Dow Chemical Co., Midland, MI), GLYDANT® (dimethylol- 25,5-dimethylhydantoin, Lonza, Inc, Fairlawn, NJ), GERMAL 115(imidazolidylurea, Sutton Laboratories, Chatham, NJ), GERMAL II (diazolidinylurea, Sutton Laboratories, Chatham, NJ), sodium hydroxymethylglycinate, BUSAN 1504 (dimethhydroxymethyl pyrazole, Buckman Labs, Memphis, TN), phenoxyethanol, and benzoyl peroxide.

4. The topical composition of claim 1 wherein the carrier is selected from the group consisting of cold cream (USP), hydrophilic ointment (USP), and an emulsion of mineral oil and purified water, wherein the emulsion is oil-in-water with a ratio of oil to water about 1-15 to 99-85 or water-in-oil with a ratio of water to oil about 1-15 to 99-85.

5. The topical composition of claim 2 wherein one or more emulsifying agents are selected from the group consisting of polyoxyethylene oleyl ether, PEG-40 stearate, ceteareth-12, ceteareth-20, ceteareth-30, LANETTE® 0 (Cetearyl Alcohol, Henkel), glyceryl monostearate, PEG-100 stearate, methyl myristate, isopropyl myristate, glyceryl stearate, steareth-2 and steareth-20, dimethicone copolyol, Polysorbate 20 (Tween 20), Polysorbate 40 (Tween 40), Polysorbate 60 (Tween 60), Polysorbate 80 (Tween 80), lauramide DEA, cocamide DEA, and cocamide MEA, Phospholipid PTC, alginate, carrageenan, Glucate DO, methylcellulose, polyvinyl alcohol, Cocamidopropyl phosphatidyl PG-dimonium chloride, PEMULEN TR 1, PEMULEN TR 2, CARBOPOL 1342, CARBOPOL 1382, Carbomer 1342, Carbomer 934, Carbomer 934P, Carbomer 940, Carbomer 941, Carbomer 974P, Carbomer 980, and Carbomer 981.

6. The topical composition of claim 4 wherein the carrier further comprises one or more components selected from the group consisting of glycerin, glycerol, propylene glycol, hexylene glycol, gelatin, urea, stearate NF, polysorbate 60, polyglyceryl-3-oleate, sorbitol solution (USP), microcrystalline wax, white petrolatum, xanthen gum, PEG 20 Cetostearyl Ether, cetostearyl alcohol, PEG, cyclomethicone, demethiconol, dimethicone copolyol, hydroxyoctacosanyl hydroxy stearate, methoxy PEG-22/dodecylglycol copolymer, prop-2-enoic acid, docusate sodium, trolamine NF, 2-methylbutanoic acid, poyoxomer 407, triolein, and egg yolk phospholipids.

7. The topical composition of claim 2 wherein the pH of composition is between about 3.5 to about 4.5.

8. The topical composition of claim 7 wherein the flucytosine comprises from about 0.3% to about 20% (wt. % to wt. %).

9. The topical composition of claim 7 wherein the poly (lactic acid) comprises from about 10% to about 20% (wt. % to wt. %) of the composition.

10. The topical composition of claim 2 wherein the flucytosine and poly(lactic acid) form aggregation complexes.

11. A therapeutically effective dosage of the topical composition of claim 1, wherein the dosage comprises about 0.3 g to about 2 g of flucytosine.

* * * * *